US009547940B1

United States Patent
Sun et al.

(10) Patent No.: US 9,547,940 B1
(45) Date of Patent: Jan. 17, 2017

(54) SYSTEMS AND METHODS FOR PROVIDING AUGMENTED REALITY IN MINIMALLY INVASIVE SURGERY

(71) Applicants: Yu Sun, Tampa, FL (US); Jaime E. Sanchez, Tampa, FL (US); Xiaoning Qian, Austin, TX (US); Bingxiong Lin, Tampa, FL (US)

(72) Inventors: Yu Sun, Tampa, FL (US); Jaime E. Sanchez, Tampa, FL (US); Xiaoning Qian, Austin, TX (US); Bingxiong Lin, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/852,501

(22) Filed: Sep. 12, 2015

Related U.S. Application Data

(60) Provisional application No. 62/049,527, filed on Sep. 12, 2014.

(51) Int. Cl.
| | | |
|---|---|---|
| *G06T 19/00* | (2011.01) | |
| *G06T 7/00* | (2006.01) | |
| *G06T 15/60* | (2006.01) | |
| *G06T 17/00* | (2006.01) | |

(52) U.S. Cl.
CPC ............ *G06T 19/006* (2013.01); *G06T 7/004* (2013.01); *G06T 15/60* (2013.01); *G06T 17/00* (2013.01); *G06T 2207/10012* (2013.01); *G06T 2207/10081* (2013.01); *G06T 2207/30004* (2013.01); *G06T 2210/41* (2013.01)

(58) Field of Classification Search
None
See application file for complete search history.

(56) References Cited

U.S. PATENT DOCUMENTS

| 7,480,402 B2 | 1/2009 | Bar-Zohar et al. |
| 8,504,136 B1 | 8/2013 | Sun et al. |
| 2006/0281971 A1* | 12/2006 | Sauer ............... A61B 19/52 600/109 |
| 2008/0123927 A1* | 5/2008 | Miga ............... G06T 7/0032 382/131 |

(Continued)

FOREIGN PATENT DOCUMENTS

WO    WO2005120193    12/2005

OTHER PUBLICATIONS

Shuhaiber, Jeffrey, "Augmented Reality in Surgery", 2004 American Medical Association.

(Continued)

*Primary Examiner* — James A Thompson
(74) *Attorney, Agent, or Firm* — Thomas | Horstemeyer, LLP

(57) ABSTRACT

In one embodiment, a method for providing augmented reality in minimally invasive surgery includes capturing pre-operative image data of internal organs of a patient, capturing intra-operative image data of the internal organs with an endoscope during a surgical procedure, registering the pre-operative image data and the intra-operative data in real time during the surgical procedure, tracking the position and orientation of the endoscope during the surgical procedure, and augmenting the intra-operative image data captured by the endoscope in real time with a rendering of an internal organ of the patient.

19 Claims, 7 Drawing Sheets

(56) References Cited

U.S. PATENT DOCUMENTS

| | | | |
|---|---|---|---|
| 2010/0118124 A1* | 5/2010 | Kim | A61B 8/483 |
| | | | 348/46 |
| 2011/0044521 A1* | 2/2011 | Tewfik | G06K 9/6206 |
| | | | 382/131 |
| 2011/0069159 A1 | 3/2011 | Soler et al. | |
| 2012/0053408 A1* | 3/2012 | Miyamoto | G06T 19/20 |
| | | | 600/109 |
| 2014/0133727 A1* | 5/2014 | Oktay | G06T 7/0028 |
| | | | 382/131 |
| 2014/0301618 A1* | 10/2014 | Popovic | A61B 19/5225 |
| | | | 382/128 |

OTHER PUBLICATIONS

Fuchs, et al., "Augmented Reality Visualization for Laparoscopic Surgery", Lecture Notes in Computer Science, vol. 1496, 1998.

Lin, et al., "Vesselness based feature extraction for endoscopic image analysis", Biomedical Imaging (ISBI), 2014.

Lin, et al., "Efficient vessel feature detection for endoscopic image analysis", IEEE transactions on biomedical engineering, vol. 62, No. 4, 2015.

Lin, et al., "Dense surface reconstruction with shadows in MIS", IEEE transactions on biomedical engineering, vol. 60, No. 9, 2013.

Lin, et al., "Simultaneous tracking, 3D reconstruction and deforming point detection for stereoscope guided surgery", Spinger Link, 2013.

Balslev I, Harling H. Sexual dysfunction following operation for carcinoma of the rectum. Dis Colon Rectum. Dec. 1983;26(12):785-8.

J.M. Blackall, G.P. Penney, A.P. King, D.J. Hawkes, "Alignment of sparse freehand 3-D ultrasound with preoperative images of the liver using models of respiratory motion and deformation," IEEE Trans Med Imaging, 24(11):1405-1416, 2005.

L.G. Brown, "A survey of image registration techniques," ACM Computing Surveys, 24:325-376, 1992.

Burschka, et al., "Scale-invariant registra-tion of monocular endoscopic images to ct-scans for sinus surgery", Medical Image Analysis 9(5) (2005) 413-426.

G. Chen, L. Gu, L. Qian, and J. Xu, "An improved level set for liver segmentation and perfusion analysis in MRIs," IEEE Trans Inf Technol Biomed, 13(1):94-103, 2009.

H. Chui, L. Win, R. Schultz, J. Duncan, A. Rangarajan, "A unified non-rigid feature registration method for brain mapping," Med Image Anal, 7:113-130, 2003.

W. Liu, et al., A clinical pilot study of a modular video-CT augmentation system for image-guided skull base surgery, SPIE Medical Imaging, 8316-112, 2012.

Longo WE, Virgo KS, Johnson FE, Wade TP, Vernava AM, Phelan MA, et al. Outcome after proctectomy for rectal cancer in Department of Veterans Affairs Hospitals: a report from the National Surgical Quality Improvement Program. Ann Surg. Jul. 1998;228(1):64-70.

D. G. Lowe, "Distinctive Image Features from Scale-Invariant Keypoints", International Journal of Computer Vision, 60, 2, pp. 91-110, 2004.

J.B. Maintz, J and M.A. Viergever, "A survey of medical image registration," Med Image Anal, 1(2): 1-37, 1998.

D. Mirota, et al., "A system for video-based navigation for endoscopic endonasal skull base surgery," IEEE Trans. Med. Imaging 31(4) (2012) 963-976.

A. Myronenko and X. Song, "Point set registration: coherent point drift," IEEE Trans Pattern Anal Mach Intell, 32 (12):2262-2275, 2010.

R.A. Newcombe, A.J. Davison, "Live dense reconstruction with a single moving camera," Computer Vision and Pattern Recognition (CVPR), 2010 IEEE Conference on , vol., No., pp. 1498,1505, Jun. 13-18, 2010.

Clinical Outcomes of Surgical Therapy Study Group . A comparison of laparoscopically assisted and open colectomy for colon cancer. N Engl J Med. May 13, 2004;350(20):2050-9.

X. Qian, H.D. Tagare, Z. Tao, "Segmentation of rat cardiac ultrasound images with large dropout regions," In Mathematical Methods in Biomedical Image Analysis (MMBIA), IEEE Computer Society Conference on Computer Vision and Pattern Recognition (CVPR), New York, NY, 2006.

7. Delacroix SE Jr., Winters JC. Urinary tract injures: recognition and management. Clin Colon Rectal Surg. Jun. 2010;23(2):104-12.

O. Ecabert, J. Peters, H. Schramm, et al., "Automatic model-based segmentation of the heart in CT images," IEEE Trans Med Imaging, 27(9):1189-1201, 2008.

Feroci F, Kröning KC, Lenzi E, Moraldi L, Cantafio S, Scatizzi M. Laparoscopy within a fast-track program enhances The short-term results after elective surgery for resectable colorectal cancer. Surg Endosc. Sep. 2011;25(9):2919-25. Epub Mar. 18, 2011.

H. Fuchs, et al., Augmented Reality Visualization for Laparoscopic Surgery, Proceedings of the First International Conference on Medical Image Computing and Computer-Assisted Intervention, 934-943, 1998.

O. Gloger, J. Kuhnb, A. Stanskic, H. Volzkea, and R. Pulsb, "A fully automatic three-step liver segmentation method on LDA-based probability maps for multiple contrast MR images," Magn Reson Imaging, 28(6):882-897, 2010.

T. Heimann and H.P. Melnzer, "Statistical shape models for 3D medical image segmentation: a review," Med Image Anal, 13(4):543-63, 2009.

Hojo K, Sawada T, Moriya Y. An analysis of survival and voiding, sexual function after wide iliopelvic lymphadenectomy in patients with carcinoma of the rectum, compared with conventional lymphadenectomy. Dis Colon Rectum. Feb. 1989;32(2):128-33.

M. Holden, "A review of geometric transformations for nonrigid body registration," IEEE Trans Med Imaging, 27 (1)111-128, 2008.

M. Izadi and P. Saeedi, "Robust weighted graph transformation matching for rigid and nonrigid image registration," IEEE Trans Image Process, 21(10):4369-4382, 2012.

B. Jian and B.C. Vemuri, "Robust point set registration using Gaussian mixture models," IEEE Trans Pattern Anal Mach Intell, 33(8):1633-1645, 2011.

Koopmann MC, Heise CP. Laparoscopic and minimally invasive resection of malignant colorectal disease. Surg Clin North Am. Oct. 2008;88(5):1047-72, vii.

Magheli A, Knoll N, Lein M, Hinz S, Kempkensteften C, Gralla O. Impact of fast-track postoperative care on intestinal Function, pain, and length of hospital stay after laparoscopic radical prostatectomy. J Endourol. Jul. 2011;25(7):1143-7.

Enker WE, Thaler HT, Cranor ML, Polyak T. Total mesorectal excision in the operative treatment of carcinoma of the rectum. J Am Coll Surg. Oct. 1995;181(4):335-46.

Havenga K, Enker WE, McDermott K, Cohen AM, Minsky BD, Guillem J. Male and female sexual and urinary function after total mesorectal excision with autonomic nerve preservation for carcinoma of the rectum. J Am Coll Surg. Jun. 1996;182(6):495-502.

Neal DE, Williams NS, Johnston D. A prospective study of bladder function before and after sphincter-saving resections for low carcinoma of the rectum. Br J Urol. Dec. 1981;53(6):558-64.

Van Bree S, Vlug M, Bemelman W, Hollmann M, Ubbink D, Zwinderman K, de Jonge W, Snoek S, Bolhuis K, van der Zanden E, The F, Bennink R, Boeckxstaens G. Faster recovery of gastrointestinal transit after laparoscopy and fast-track care in patients undergoing colonic surgery. Gastroenterology. Sep. 2011;141(3):872-880.e1-4. Epub May 26, 2011.

Zaheer S, Pemberton JH, Farouk R, Dozois RR, Wolff BG, Ilstrup D. Surgical treatment of adenocarcinoma of the rectum. Ann Surg. Jun. 1998;227(6):800-11.

M. Kass, A. Witkin, D. Terzopoulos, "Snakes: Active contour models," Inter J Computer Vision, 4(1):321-331, 1988.

G. Klein and D. W. Murray. Parallel tracking and mapping for small AR workspaces. In Proceedings of the International Symposium on Mixed and Augmented Reality (ISMAR), 2007.

(56) References Cited

OTHER PUBLICATIONS

E. Rosten; T. Drummond, "Machine learning for high-speed corner detection". European Conference on Computer Vision 1: 430-443, 2006.
Rothenberger DA, Wong WD. Abdominoperineal resection for adenocarcinoma of the low rectum. World J Surg. May-Jun. 1992;16(3):478-85.
Shekhar R, Dandekar O, Bhat V, Philip M, Lei P, Godinez C, Sutton E, George I, Kavic S, Mezrich R, Park A. Live augmented reality: a new visualization method for laparoscopic surgery using continuous volumetric computed tomography. Surg Endosc. Aug. 2010;24(8):1976-1985.
F. Volonté, et al., Augmented reality and image overlay navigation with OsiriX in laparoscopic and robotic surgery: not only a matter of fashion, J Hepatobiliary Pancreat Sci., 8(4):506-9, 2011.
3DSlicer, http://www.slicer.org, 2015.
SpaceNavigator, http://www.3dconnexion.com/products/spacenavigator.html, 2015.
Rayburn, William, "Complications of Flysterocopic and Uterine Resectoscopic Surgery" ResearchGate, Sep. 2010.

* cited by examiner

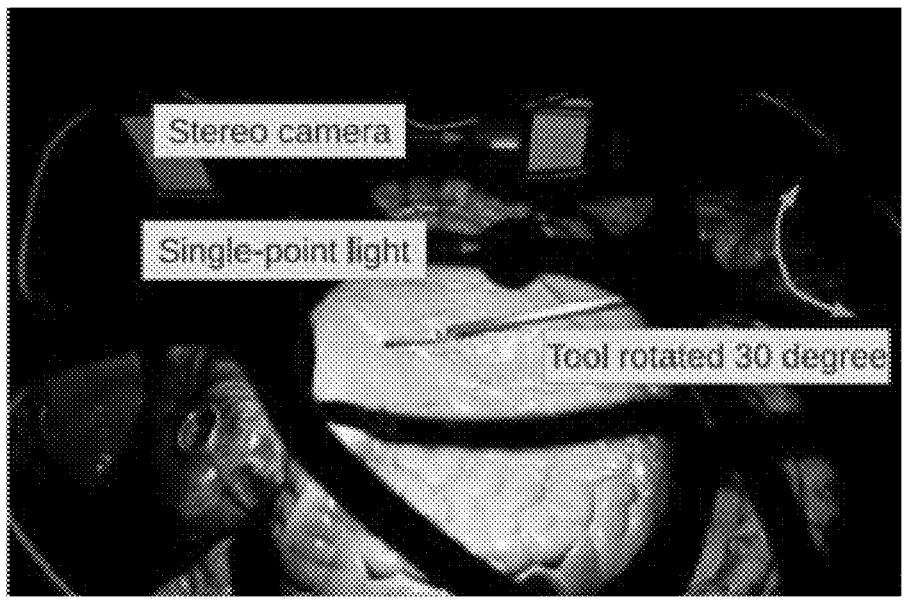
FIG. 4
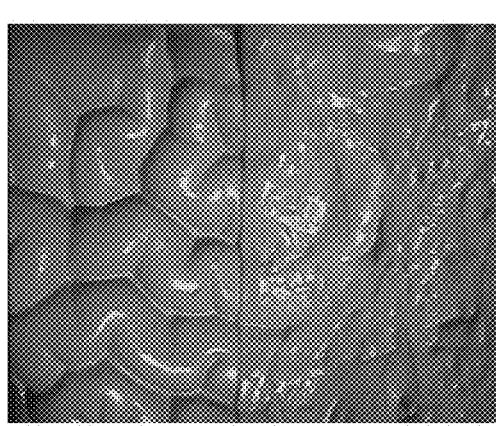 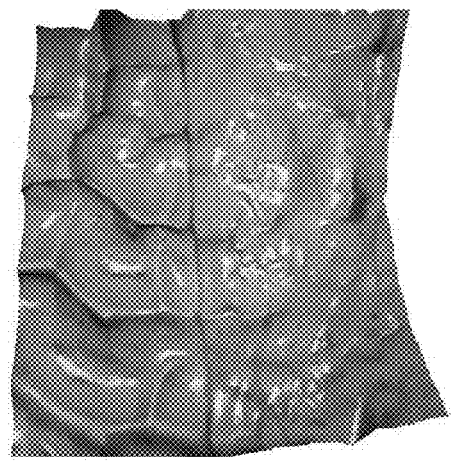
FIG. 5A  FIG. 5B

SYSTEMS AND METHODS FOR PROVIDING AUGMENTED REALITY IN MINIMALLY INVASIVE SURGERY

CROSS-REFERENCE TO RELATED APPLICATION

This application claims priority to U.S. Provisional Application Ser. No. 62/049,527, filed Sep. 12, 2014, which is hereby incorporated by reference herein in its entirety.

NOTICE OF GOVERNMENT-SPONSORED RESEARCH

This invention was made with Government support under grant/contract number 1035594, awarded by the National Science Foundation. The Government has certain rights in the invention.

BACKGROUND

Minimally invasive surgery (MIS) generally refers to the use of laparoscopy in addition to other techniques that reduce trauma by limiting the size of the operative incision. Application of these concepts has led to an overall reduction in post-operative pain, improved recovery, and decreased utilization of medical resources in the perioperative period of many operations. Furthermore, as the physiologic state appears to be less altered following MIS, the establishment of fast-track protocols have enabled patients to meet the criteria for discharge from the hospital significantly sooner due to improved recuperation of bowel function following abdominal surgery.

From a purely technical standpoint, laparoscopic surgery also provides certain advantages over open surgery. In the abdomen or pelvis, carbon dioxide gas is used to insufflate the abdomen in order to expand the working space within the peritoneal cavity and provide exposure of the operative field. At times, the visualization provided by the laparoscope is far superior to that seen by the surgeon in a traditionally open operation. Dissection of fine tissues can be performed meticulously while inspecting the structures of interest at a very near distance. This is especially true in cases of pelvic surgery where the laparoscope is able to enter, illuminate, and provide magnified views of spaces that are not generally in the direct line of sight for the surgeon.

Laparoscopy, however, is hindered by several limitations. One of these limitations is that tactile feedback of the internal anatomy is nearly eliminated when the surgeon cannot place a hand in the body cavity, limiting the identification of structures that are not visible within the peritoneal cavity, such as those that lie within the retroperitoneum and pelvis, which may have been otherwise recognized by feel. In addition, although the magnified view provided by laparoscopy offers excellent inspection of objects to the front of the camera, it drastically limits the field of view and does not allow visualization of the areas outside of the forward optical axis.

When vital anatomical structures are not found, or perhaps worse when they are misidentified, serious and even life threatening injury may occur. These complications include urinary tract injury, sexual or urinary dysfunction, infertility, and bleeding. Ureter injury, which is the most common intraoperative complication of pelvic surgery, occurs at a rate of about 1 to 10%. However, post-operative urinary and sexual dysfunction can occur at alarming rates, up to 100% in some studies, when resection is undertaken in the pelvis for cancer. In some rare instances, death may occur due to exsanguination from loss of orientation and inadvertent injury of the aorta, inferior vena cava, iliac, or gonadal vessels.

Augmented reality typically refers to the addition of computer-generated data to the real world in order to enhance situational awareness. Various approaches for visualization in image-guided interventions have been proposed to apply the concept of augmented reality and show anatomical structures on the laparoscope video. However, these systems remain crude in their anatomic modeling, alignment, and tracking. The majority of successful applications are in rigid settings and structures and use external motion tracking devices to track the laparoscope. More practical applications of simple two-dimensional image guided surgery are currently employed almost exclusively in maxillofacial and neurosurgery where the bony structures of the skull are used as landmarks for registration and reference. However, registration of images without the use of bony landmarks or placement of markers is complex. Non-rigid settings and deformable structures are encountered in laparoscopic abdominal surgery where external tracking becomes unreliable due to frequent occlusions.

From the above discussion, it can be appreciated that it would be desirable to have an improved augmented reality system and method for minimally invasive surgery procedures that do not rely upon rigid anatomical structures or external tracking devices.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 4 is an image of a model of organs of the abdominal cavity that illustrates how a shadow is cast on the surface of the organs for purposes of reconstructing a three-dimensional surface model of the organs.

FIGS. 5A and 5B illustrate an example of reconstruction of an internal organ using the shadow-based three-dimensional surface reconstruction method.

DETAILED DESCRIPTION

Figure 1:
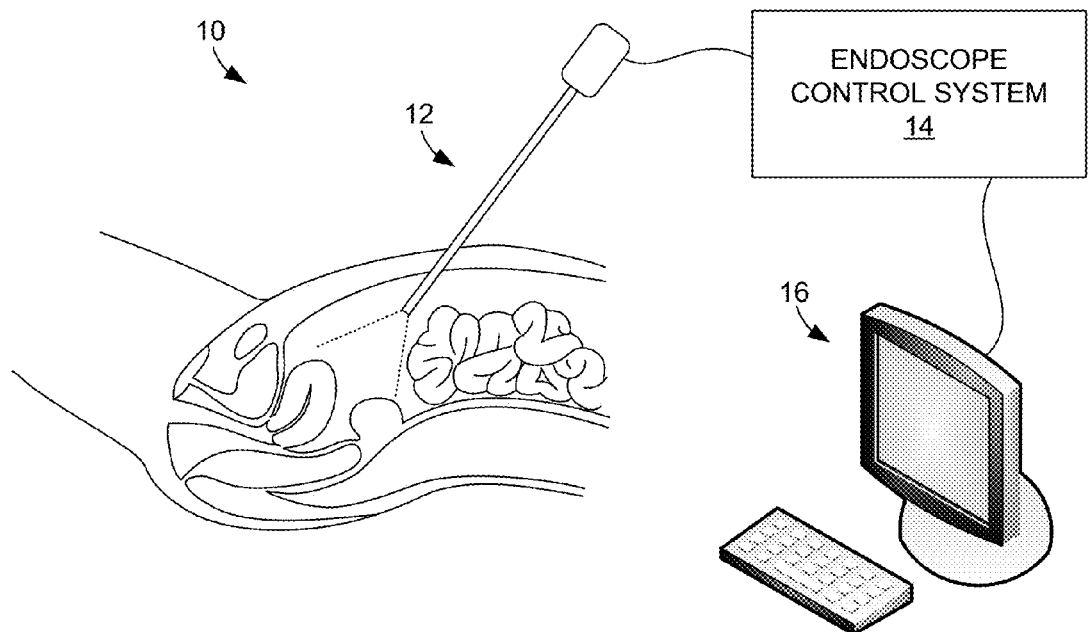
FIG. 1 is a schematic diagram of an embodiment of a minimally invasive surgery system that utilizes augmented reality.

As described above, it would be desirable to have an improved augmented reality system and method for minimally invasive surgery (MIS) procedures that does not rely upon rigid anatomical structures or external tracking devices. Examples of such systems and methods are described herein. In some embodiments, pre-operative image data, such as computed tomography (CT) image data, is captured in advance of a surgical procedure and is later registered in real time with intra-operative image data captured with an endoscope, such as a laparoscope, during an endoscopic (e.g., laparoscopic) procedure. Renderings of certain organs, such as deformable organs of the abdominal cavity, that are not visible to the surgeon in the intra-operative image data, can be combined with the intra-operative image data to provide an augmented reality environment that assists the surgeon in knowing the positions of these organs so they can be located or avoided. In some embodiments, the rendered organs can be adjusted in real time as the endoscope is moved relative to the patient so that the surgeon always knows the location of the organs regardless of the position of the endoscope.

In the following disclosure, various specific embodiments are described. It is to be understood that those embodiments are example implementations of the disclosed inventions and that alternative embodiments are possible. All such embodiments are intended to fall within the scope of this disclosure.

Creation of an augmented reality system that provides accurate and precisely aligned overlay images of anatomic tissues, which may be difficult to identify due to anatomical location, aberrancy, or distortion, will help guide surgeons to recognize structures of key interest and better avoid injury in MIS. However, it is technically challenging to track the area that an endoscope (e.g., laparoscope) is viewing within the body because it is usually focused on a small area of interest, which significantly impedes accurate estimation of structures obscured behind other tissues. The technology disclosed herein enables mapping and identification of hidden surgical anatomy during MIS through a visual overlay of rendered pre-operative image data that is registered to the endoscopic image data (e.g., laparoscopic video) using three-dimensional surface anatomy of the imaged internal organs. In some embodiments, this technology can be used to provide image-guided surgery, to map vascular anatomy, and to avoid injury to deep structures, such as those located in the retroperitoneum when operating in the abdomen and pelvis. To achieve an accurate overlay, real-time intra-operative three-dimensional reconstruction, three-dimensional registration, and endoscope tracking are essential.

By providing confidence in the recognition of deformable internal organs, such as ureters and blood vessels, and other anatomical features of importance in laparoscopy, the application of MIS to increasingly complex problems will likely be more readily accepted. In addition, the morbidity of iatrogenic injury to the urinary, vascular, and nervous systems will be decreased, allowing the benefits of MIS to be extended to patients who would otherwise have received open operations due to a prohibitively high risk of injury. It is hoped that the availability of this technology will produce a paradigm shift in which surgeons instinctively embrace the assistance of patient-specific image overlay mapping to enhance technical performance and outcomes of their laparoscopic procedures.

FIG. 1 illustrates an embodiment of a minimally invasive surgery system 10 that utilizes augmented reality. As shown in the figure, the system 10 generally comprises a endoscope 12, which can be a laparoscope, an endoscope control system 14 to which the endoscope is connected, and a computing device 16 to which the endoscope control system is connected. As shown in FIG. 1, the endoscope 12 can be inserted into the body of a patient and image data (i.e., still images and/or video) of the internal organs can be obtained. In the case of laparoscopy, the endoscope (laparoscope) 12 can be inserted into the abdominal cavity of the patient.

Figure 2:
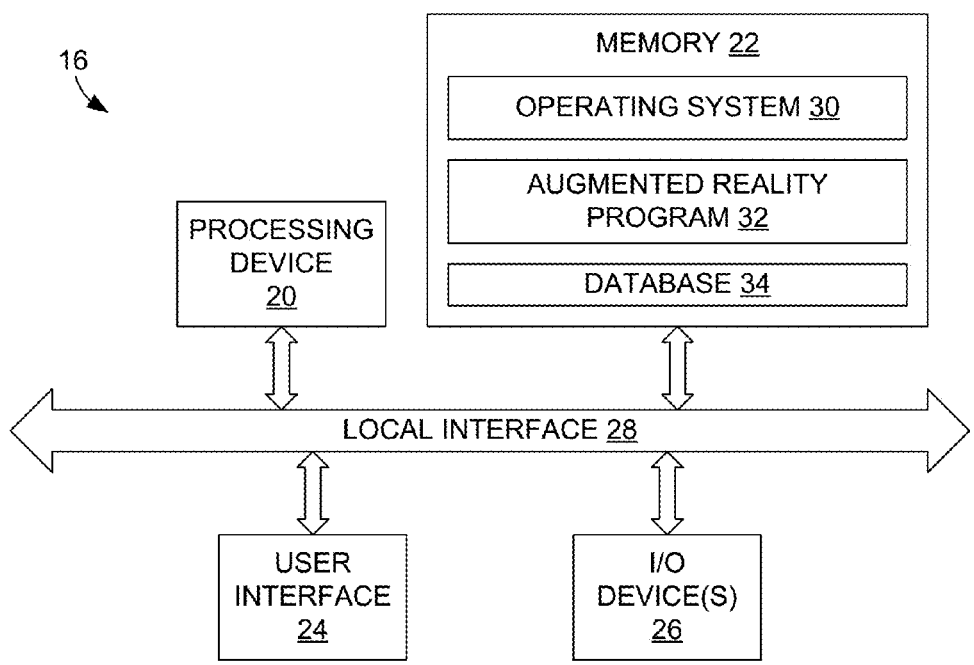
FIG. 2 is a block diagram of an embodiment for a computing device shown in FIG. 1.

The computing device receives the image data captured by the endoscope 12 and manipulates it to provide an augmented reality environment for the surgeon. Although the computing device 16 is depicted in FIG. 1 as a desktop computer, it is noted that the computing device can comprise any device having adequate computing capabilities, such as a laptop computer, a tablet computer, or the like. FIG. 2 illustrates an example configuration for the computing device 16. As shown in this figure, the computing device 16 includes a processing device 20, memory 22, a user interface 24, and at least one I/O device 26, each of which is connected to a local interface 28.

The processing device 20 can include a central processing unit (CPU) or a semiconductor-based microprocessor (in the form of a microchip). The memory 22 includes any one of or a combination of volatile memory elements (e.g., RAM) and nonvolatile memory elements (e.g., hard disk, ROM, Flash, etc.). The user interface 24 comprises the components with which a user interacts with the computing device 16, such as a keyboard, keypad, and/or display screen, and the I/O devices 26 are adapted to facilitate communications with other devices. Notably, the display screen can, in some embodiments, be used to display augmented intra-operative image data to the surgeon.

The memory 22 (a non-transitory computer-readable medium) comprises programs (logic) including an operating system 30 and an augmented reality program 32 that merges renderings obtained from pre-operative image data with intra-operative image data obtained using an endoscope in real time. Examples of the manner in which such a result is achieved are described below. In addition, the memory 22 comprises a database 34 that can include various data used by the augmented reality program, such as stored pre-operative image data and/or pre-operative three-dimensional surface models of the patient's internal organs.

Figure 3:
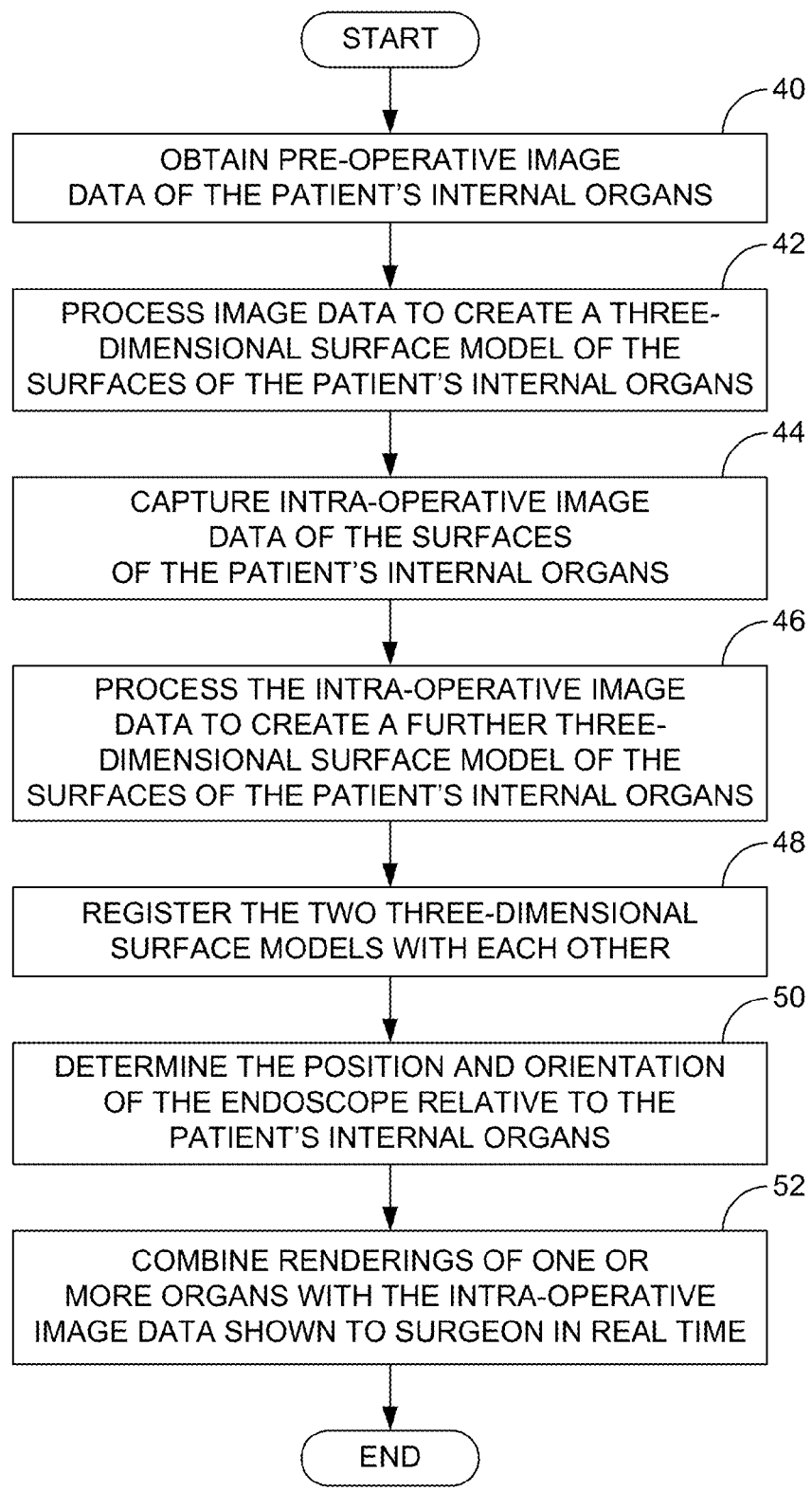
FIG. 3 is a flow diagram of a first embodiment of a method for providing augmented reality during minimally invasive surgery.

Intra-operative image data, such as laparoscopic images and video, can be augmented to include renderings of obscured organs in a variety of ways. FIG. 3 illustrates a first embodiment of a method for providing such augmented image data. Beginning with block 40 of FIG. 3, pre-operative image data of the patient's internal organs is obtained. By way of example, computed tomography (CT) image data is captured of the patient. Notably, such data is often collected prior to an abdominal surgical procedure to determine whether or not surgery is necessary and, if so, to help plan the surgery. Once the image data has been captured, it can be processed to create a three-dimensional surface model of the surfaces of the patient's internal organs prior to surgery, as indicated in block 42. In the case in which abdominal surgery is to be performed, the surfaces can be the surfaces of multiple deformable organs of the abdominal cavity, such as the liver, stomach, intestines, bladder, colon, etc. The model can either be generated manually or automatically. Regardless, the pre-operative three-dimensional surface model that results identifies the patient's organs and their locations within the body and can be stored for later use. In particular, the model can be used to generate in real time renderings of one or more of the organs to be combined with intra-operative image data (e.g., video) captured with an endoscope during surgery.

Referring next to block 44, intra-operative image data of the visible surfaces of the patient's internal organs can be captured using an endoscope during the surgical procedure. In the case of abdominal surgery, the abdominal cavity can be insufflated and a laparoscope can be inserted into the cavity to capture intra-operative image data (e.g., video) of the surfaces of the visible organs. Once it has been captured, the intra-operative image data can be processed to create a further three-dimensional surface model of the visible surfaces of the patient's internal organs, as indicated in block 16.

A variety of methods can be used to create the aforementioned three-dimensional surface model based upon the intra-operative image data. In some embodiments, the surfaces can be reconstructed using a shadow-based three-dimensional surface reconstruction method. Although several feature-based three-dimensional surface reconstruction methods exist, they often do not perform well when the scene has few readily distinguishable features, as in the case of the internal organs. Shadows, however, can significantly improve depth perception. In the shadow-based three-dimensional surface reconstruction method, weakly structured light is used to illuminate the patient's internal organs and images are captured with a stereoscopic camera (or two non-stereoscopic cameras) separated from the light source while an object, such as a surgical instrument, is swept between the light source and the organs so as to cast a shadow of the instrument onto the organs that travels across their various contours. Such a process is illustrated in the image of FIG. 4, which shows a model of the internal organs of the abdominal cavity and a surgical instrument being swept over the organs. A series of images containing shadows can be obtained and the shadow boundaries can be extracted and used as shadow curve correspondences between two corresponding images. Epipolar lines can then be calculated and used to intersect with the shadow curves to efficiently generate precise point correspondences along the curve pairs from the two images. The accuracy of the point correspondences can be further improved to sub-pixel accuracy by using interpolation. Next, a field surface interpolation (FSI) approach can be used to obtain the points that lie between two shadow curves by exploiting both spatial and stereo calibration information to generate dense correspondences between the two images, which are used to recover the organ surfaces.

Notably, the above-described shadow-based three-dimensional surface reconstruction method does not rely on organ texture information and is able to reconstruct accurate three-dimensional information by exploiting only the shadows cast by the surgical instrument on the organs' surfaces as the instrument is manipulated by the surgeon. Advantages of this method include the point correspondences being directly calculated and no explicit stereo matching being required, which ensures efficiency of the method, as well as a minimal hardware requirement because only a stereo camera and a separated single-point light source being required. This approach was evaluated using both phantom models and ex vivo images. For example, as shown in FIG. 5, a plastic intestine model (FIG. 5A) was reconstructed to create a three-dimensional surface model with texture mapping (FIG. 5B). Precision of the recovered three-dimensional surfaces to within 0.7 mm was achieved for the phantom models and 1.2 mm for the ex vivo images during experimentation. The comparison of disparity maps indicates that the shadow-based method significantly outperformed the state-of-the-art stereo algorithms for MIS. Further information about shadow-based three-dimensional surface reconstruction is provided in "Dense Surface Reconstruction with Shadows in MIS," by Lin et al., *IEEE Transactions on Biomedical Engineering*, vol. 60, no. 9, pp. 2411-2420 (2013), which is hereby incorporated by reference into the present disclosure.

At this point in the process, two three-dimensional surface models of the patient's internal (e.g., abdominal cavity) organs have been generated, one based upon the pre-operative image data and one based upon the intra-operative image data captured with an endoscope, such as a laparoscope. With reference next to block 48 of FIG. 3, the two models can be registered with each other. Various methods can be used to perform this registration. In some embodiments, iterative closest point (ICP) registration is used to obtain a coarse registration of the models and then manual tuning can be performed to more finely register them.

Once the two models are registered, the locations of internal organs that are obscured or outside of the endoscope's field of view can be identified and renderings of these organs can be added to this intra-operative image data in real time to show the locations of the organs to the surgeon. Before this can be achieved, however, the position and orientation of the endoscope relative to the patient's internal organs must be known. Accordingly, as indicated in block 50 of FIG. 3, the position and orientation of the endoscope relative to the patient's internal organs are determined in order to know where to show the obscured or out of field organs relative to the intra-operative image data captured by the endoscope. The position and orientation of the endoscope can be determined at any given time by continuously tracking the endoscope throughout the surgical procedure. While such tracking can be performed using an external tracking device, it is preferred to perform this tracking without using an external tracking device. In some embodiments, a blood vessel-based feature detection method is used in which blood vessel branch points and segments on the surface of the internal organs are detected can be used to track the endoscope.

As noted above, MIS images are generally low texture. In addition, the contain abundant reflections, homogeneous areas, smokes, etc., which make feature detection difficult. Blood vessels, which are abundant on the surface of soft tissue organs such as the abdominal wall, stomach, small intestines, and colon, can be more easily extracted and used for purposes of feature detection. Such vessels can be represented as curves, which are more robust than points in camera motion estimation. In addition, because the vessels are attached to the surface of the internal organs and deform with them, the detection of vessels enables recovery of tissue deformations.

Figure 6:
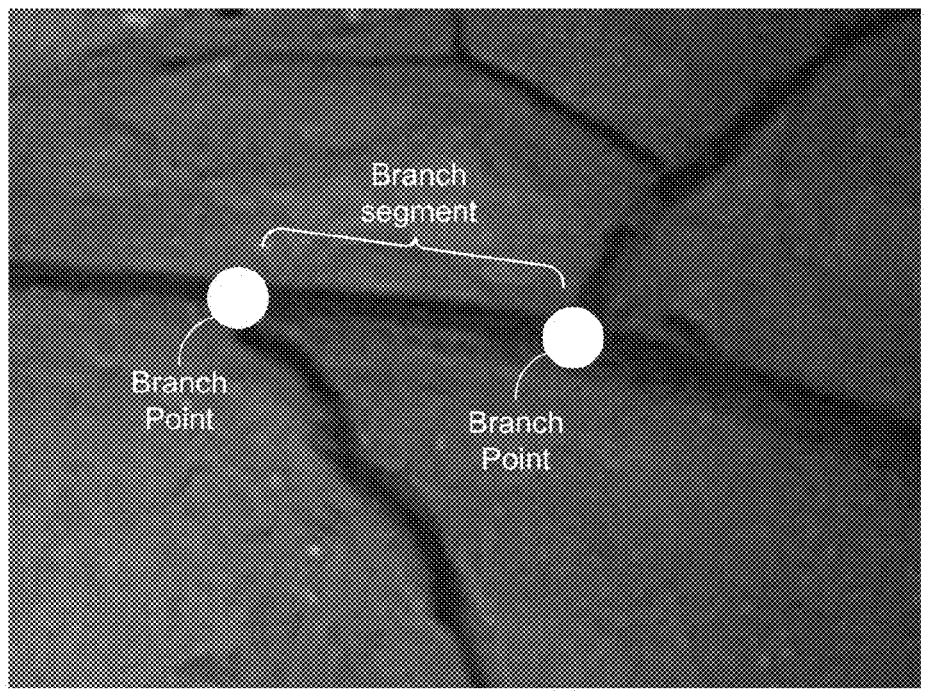
FIG. 6 is a laparoscope image of an internal organ illustrating detection of blood vessel branch points and segments for purposes of tracking the position and orientation of an endoscope relative to the organ.

Two types of blood vessel features are used in the blood vessel-based feature detection method: vessel branching points at which the vessels bifurcate or cross and vessel branching segments that have branching points at each end. An example of branching points and a branching segment defined by the branching points is shown in FIG. 6. The branching segments are essentially curve segments and a pair of branch segment correspondence can generate tens of pairs of point correspondences.

In the blood vessel-based feature detection method, a captured endoscope image is first pre-processed. Such pre-processing can be performed to, for example, remove specular reflections. Once the image has been pre-processed, a Hessian matrix can be calculated for each pixel of the image. The Hessian matrices can then be used to calculate the Frangi vesselness to enhance the blood vessels. In addition or in exception, ridgeness can be computed, which also enhances the blood vessels. During ridgeness analysis, ridge pixels that achieve single-pixel width are identified as the ridge in a two-dimensional image is a good approximation of the vessel center line. Through this analysis, a ridgeness image can be created.

Next, the vessel branching points can be detected. In some embodiments, the branching points are detected using a circle test in which a circle is centered at each candidate point on the ridgeness image and the ridgeness value and intensity of each point is examined along the circle to determine whether it is a branching point or not. In some embodiments, points that pass the circle test but are considered too close to each other to be vessel branching points are suppressed using a non-maximal suppression process.

Figure 7:
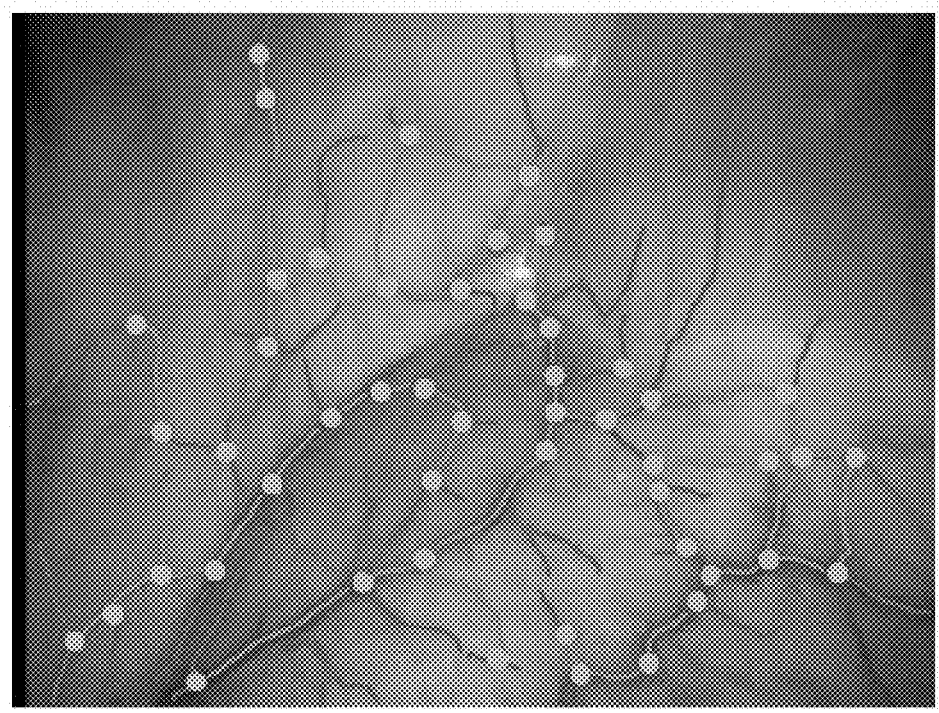
FIG. 7 is a laparoscope image of an internal organ whose blood vessels have been mapped using vessel-based image feature detection.

Once the vessel branching points have been detected, a vessel tracing process can be performed to link the branching points and identify the vessel branching segments. The vessel tracing process can be based on a binary mask of the vessels, referred to as a ridge mask, which is obtained by thresholding the ridgeness image. A typical vessel branch point and segment detection result is shown in FIG. 7.

The above-described blood vessel-based feature detection method improves the processing speed and is more reliable than other tracking methods. The method further avoids segmenting of the vessels, which is slow and uses second derivatives and circular tests that only require simple computation. Because the blood vessel-based feature detection method does not use segmentation results to detect vessel branch points, it is not affected by common segmentation errors and can produce more reliable branch points. Because the local patch of a branch point has large intensity variance, the branch points and segments are more distinctive for feature matching. Further information about the vessel segment and branch point detection method is provided in "Vesselness Based Feature Extraction for Endoscopic Image Analysis," by Lin et al., which was published at the International Symposium on Biomedical Imaging (2014), and "Efficient Vessel Feature Detection for Endoscopic Image Analysis," by Lin et al., *IEEE Transactions on Biomedical Engineering*, vol. 62, no. 4, pp. 1141-1150, (April 2015), both of which are hereby incorporated by reference into the present disclosure.

Figure 8:
FIG. 8 is an example augmented image than can be displayed during a minimally invasive surgery procedure.

Once the three-dimensional surface models have been registered and the position and orientation of the endoscope is known, renderings of one or more obscured organs (i.e., augmented reality images) can be combined or merged with (e.g., overlaid onto) the intra-operative image data (e.g., laparoscope video) shown to the surgeon in real time, as indicated in block 52 of FIG. 3. By way of example, this augmented image data can be shown to the surgeon using a monitor or a head-mounted display (HMD). FIG. 8 illustrates an example of augmented image data that can be shown to a surgeon. In this figure, the bladder and the ureter, which are not visible in the intra-operative image data captured by the endoscope, are superimposed over the endoscopic image data to show the surgeon where these organs are located.

Figure 9:
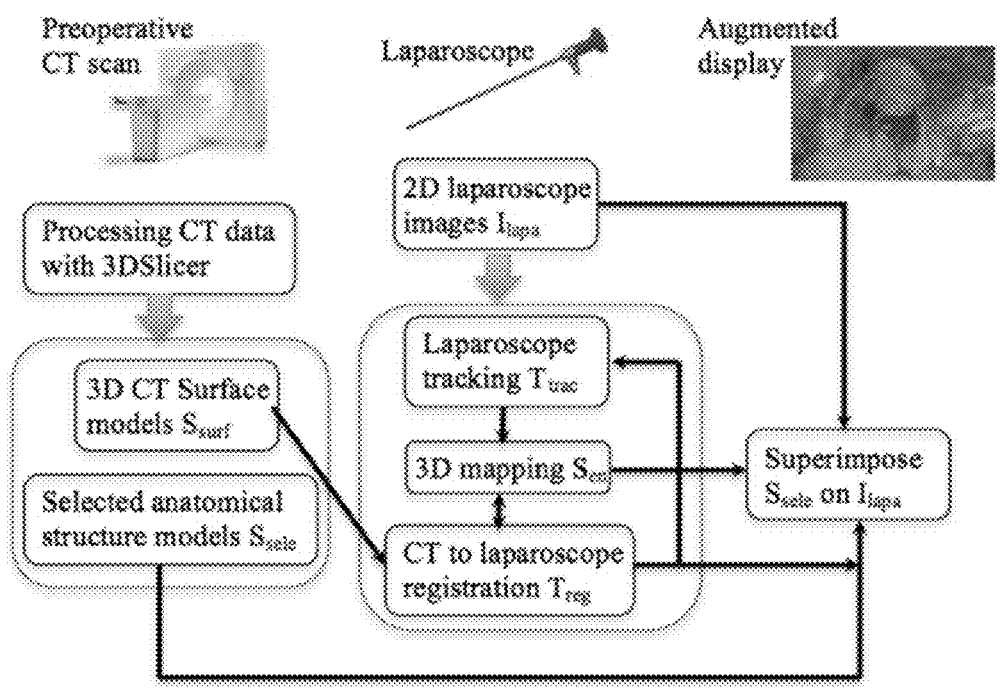
FIG. 9 is a block diagram of a simultaneous tracking, mapping, and registering system that can be used to provide augmented reality image data.

In another embodiment, real-time simultaneous endoscope (e.g., laparoscope) tracking, and mapping with pre-operative image data (e.g., CT image data) to intra-operative image data (e.g., laparoscope video) registration can be performed. Such a method involves simultaneously tracking, mapping, and registering and therefore is referred to herein as "STMR." FIG. 9 shows an example embodiment of an STMR system based upon pre-operative CT images and intra-operative laparoscope video. When STMR is used, instead of first performing surface reconstruction using the intra-operative image data as in the method of FIG. 3, tracking, mapping, and registration are simultaneously optimized using an iterative process. Such a process can track an endoscope (e.g., laparoscope) without any external tracking device, reconstruct a sparse three-dimensional structure of the tissues in the current view of the endoscope, and obtain the correct registration of the pre-operative image data and the current reconstructed three-dimensional structure. Using the registration result, the system can render and superimpose pre-operatively modeled deformable anatomical structures, such as the ureters, bladder, and arteries, on the intra-operative image data (e.g., video) in real time. As before, the augmented intra-operative image data can be displayed to the surgeon on a monitor or an HMD. In some embodiments, an interface can be provided to enable the surgical staff to select one or several anatomic structures that have been either manually or semi-automatically segmented and reconstructed from pre-operative image data using a three-dimensional slicer.

A unique aspect of STMR is the use the pre-processed three-dimensional surface models $S_{surf}$ as prior constraints when computing the sparse mapping M in a parallel tracking and mapping (PTAM) framework. STMR essentially integrates the computation of the registration $T_{reg}$ in the computing of a PTAM thread to jointly optimize the mapping and the registration. By borrowing the strengths from all the available resources in both pre-operative and intra-operative image data, STMR can be used to overcome the well-known challenges in external surface-based registration to remove ambiguity and improve efficiency. The pre-operative three-dimensional surface model can help obtain better tracking and mapping results considering that the known process of simultaneously localizing and mapping (SLAM) does not have or utilize the prior three-dimensional surface information.

Providing proper initial estimation of the registration is important for the optimization of STMR. Taking advantage of the available resources and time at the beginning of an operation, a STMR system can first obtain a dense and accurate three-dimensional surface reconstruction from the endoscope image data (e.g., laparoscope video) with shadows as described above and then compute an initial registration transformation $T_{reg}$ by comparing and matching the pre-operative surface model with this reconstructed surface. The system can then overlay the three-dimensional surface model from the pre-operative image data on the current reconstructed surface and display it on a monitor or HMD and provide a tuning interface for a surgical staff to fine tune alignment with a 3Dconnexion 6 degree-of-freedom (DOF) SpaceNavigator™.

The prior three-dimensional surface information provided by the pre-operative three-dimensional surface model $S_{surf}$ is used with the post-operative three-dimensional surface model $S_{en}$ to simultaneously optimize non-rigid registration and intra-operative mapping (sparse three-dimensional surface reconstruction) with the following objective function:

$$\min_{w, Q_i \in S_{en}} \sum_j \|Cam_j(Q_i) - u_{ij}\| + \|f(P_i; w) - Q_i\| \quad \text{[Equation 1]}$$

This mathematical formulation contains two terms. The first term represents the re-projection error with the three-dimensional point set $Q_i$ as parameters, in which $Cam_j(\bullet)$ and $u_{ij}$ denote the camera perspective projection and measured feature points for each laparoscope image, respectively. Accordingly, the first term relates to the endoscope tracking. The second term is basically the same objective function for point set registration based on the point set $P_i \in S_{surf}$ from the pre-operative CT surface model $S_{surf}$ and the point set $Q_i$ from reconstructed surface model $S_{en}$ based on the laparoscope video. Therefore, the second term relates to model registration. The transformation $f(P_i; w)$ provides the non-rigid registration from pre-operative to post-operative coordinates with parameters $w$. To solve this optimization problem to find the optimal three-dimensional point $Q_i$ and the non-rigid transformation $w$, various robust point registration methods with gradient-based search algorithms can be utilized from the initial registration obtained in the initialization step. For example, the camera perspective projection can be linearized when the update of $Q_i$ is small. An iterative solution can be obtained by optimizing registration and dense reconstruction separately. First, the registration is initialized with the global rigid registration obtained using the method in an initialization step. The intra-operative three-dimensional surface model from the endoscope is initialized with pre-operative three-dimensional surface model from the pre-operative image data (e.g., CT images), which means $S_{en} = S_{surf}$. After initialization, one can solve the optimization by two iterative updating steps: (1) Use the current registration and intra-operative three-dimensional surface model $S_{en}$ to solve the linearized problem:

$$\min_{\Delta Q_i \in S_{en}} \sum_j \|J_{Q_i}^j \cdot \Delta Q_i - \Delta u_{ij}\| \quad \text{[Equation 2]}$$

The solution to Equation 2 provides the refined surface reconstruction in the intra-operative image data (e.g., laparoscope video), which can be further used to detect deforming area. (2) With the refined post-operative three-dimensional surface model $S_{en}$, one can then apply known methods to solve the non-rigid registration from the pre-operative image data (e.g., CT images) to the intra-operative image data (e.g., laparoscopic video):

$$\min_w \|f(P_i; w) - Q_i\| \quad \text{[Equation 3]}$$

Note that the initial registration and detected deforming area are obtained from the prior iteration. With these, one can achieve more robust and efficient non-rigid registration. It should also be noted that the above objective function only involves registration and reconstruction. In fact, similar to PTAM, the tracking is separated from, and runs parallel with, the above optimization. In some embodiments, the endoscope tracking method can be performed using the blood vessel-based feature detection method, which was discussed above.

The simultaneous optimization described above is based on the fact that reconstruction from intra-operative image data and non-rigid pre-operative and intra-operative image data registration are inherently related and beneficial to each other. On the one hand, the pre-operative three-dimensional surface model and registration provide an initial intra-operative three-dimensional surface model, which can be further revised based on the endoscope observance from different positions and can be used for endoscope tracking. On the other hand, the refined intra-operative three-dimensional surface can be used to update the non-rigid registration. The previous detected deforming area obtained from tracking can further accelerate this process.

Extracting a large number of robust and well-matched features from the intra-operative image data is important to the STMR approach. The STMR system can use the algorithm described above to extract blood vessel branch points and segments. Those branch points and segments can be treated as the most reliable features and combined with other less reliable features, such as SIFT or FAST, to build a hierarchy of features. This hierarchy of features can be used and integrated into a PTAM framework for robust endoscope tracking. On the other hand, since the curved vessel branch segments are located on tissue surfaces and deform with the deformable tissues, the deformation of the branch segments reflects the tissue surface deformation and sufficiently represents the deformation in the objective function. The branch segments are more powerful features than points and can be exploited for tissue deformation detection and analysis in the non-rigid registration optimization.

Selected anatomical structures can be properly rendered after the system computes the registration transformation for that frame. FIG. 8, which was mentioned above, shows one preliminary result of an overlay with a typical ghosting technique that renders the anatomical structure 50% transparent. However, since the object has a uniform color and no shading, the rendering may lose three-dimensional effects and look flat. To avoid this, the STMR system can render texture and generate proper shading by adding lighting to simulate the light from the endoscope. To render the proper depth, the system can compute the transparency percentage according to the relative depth between the pre-operative three-dimensional surface model and the three-dimensional reconstruction of the current scene for the current frame of the intra-operative video. It is difficult to perfectly reconstruct a dense surgical scene from the endoscope video at all times. However, it may not be necessary to achieve this level of accuracy. In some embodiments, the sparse three-dimensional reconstruction of the scene can be used and the depth values can be used as samples to help one decide how deep the anatomical structure should be from the surface. If the anatomical structure is farther away from the endoscope as compared to the sparse three-dimensional samples of the scene, the anatomical structure can be rendered more transparent.

In addition to the standard user interface, the system design enables the surgeon or an assistant to interact with the system and leverage its performance with human intelligence. In some embodiments, the system provides an interface to take input from the 3Dconnexion 6 degree-of-freedom (DOF) SpaceNavigator™ and select the pre-operatively modeled anatomical structures to overlay, fine-tune the registration result at the initialization step, and make adjustments to the result of the STMR process. The interface can also enable users to turn the augmented display on and off as well as change the superimposing color, texture, and transparency.

Figure 10:
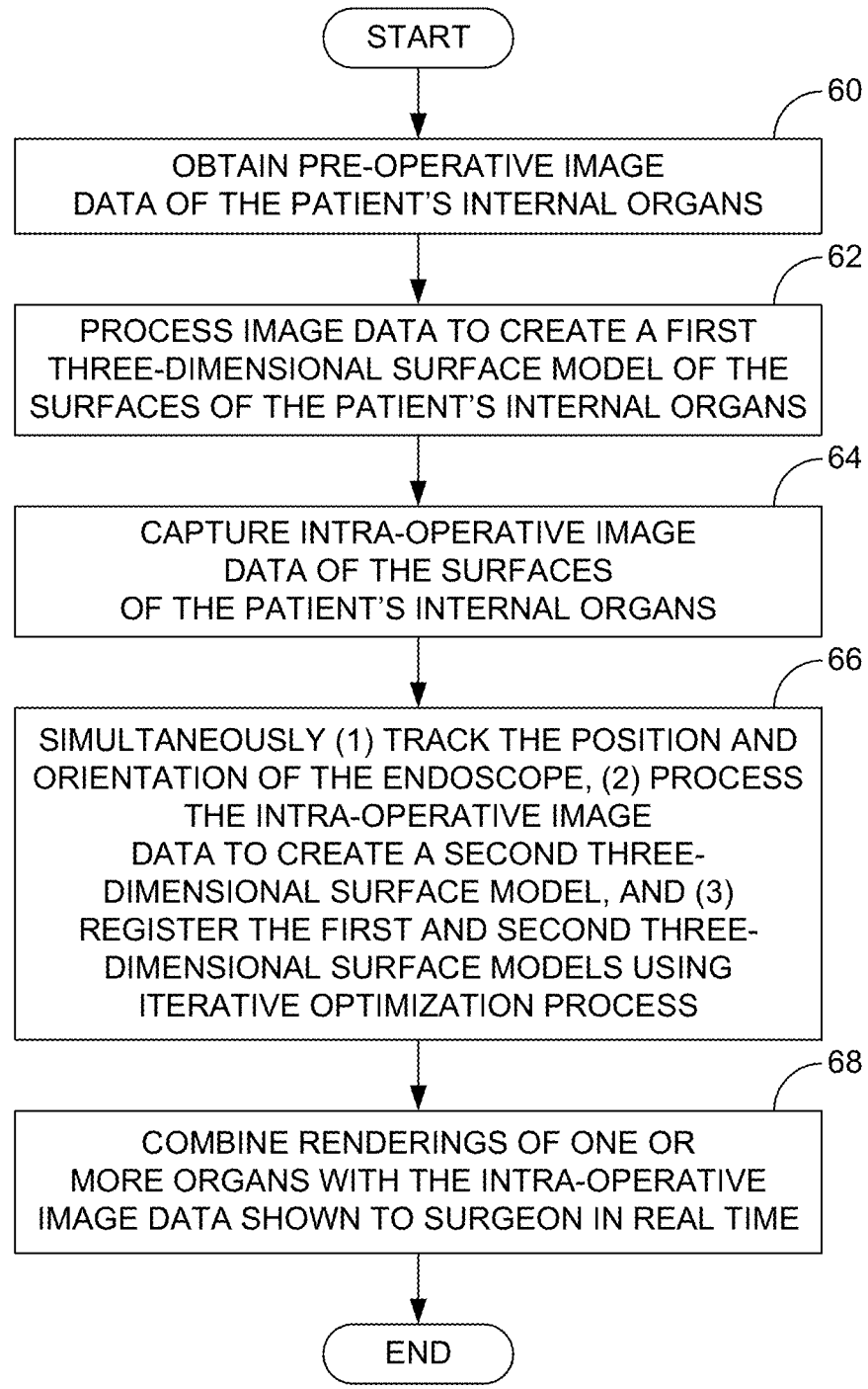
FIG. 10 is a flow diagram of a second embodiment of a method for providing augmented reality during minimally invasive surgery.

FIG. 10 is a flow diagram of an example method for performing STMR that is consistent with the above description. As in the previous method, pre-operative image data is obtained (block 60), the image data is processed to create a first three-dimensional surface model (block 62), and intraoperative image data is captured (64). Unlike the previous method, however, the method comprises simultaneously tracking the position and orientation of the endoscope, processing the intra-operative image data to create a second three-dimensional surface model, and registering the two models using the iterative optimization process described above (block 66).

In the above-described methods, renderings of organs obscured by other organs in the foreground of the intra-operating image data were described as being overlaid on top of the intra-operative image data. It is noted that the rendered organs can, alternatively or additional, be organs that are outside the field of view of the endoscope. In this way, the surgeon can see tissues that are beyond the edges of the intra-operative image data and therefore can be provided with better context for the intra-operative image data. This form of augmentation can be referred to as periphery augmentation.

Figure 11:
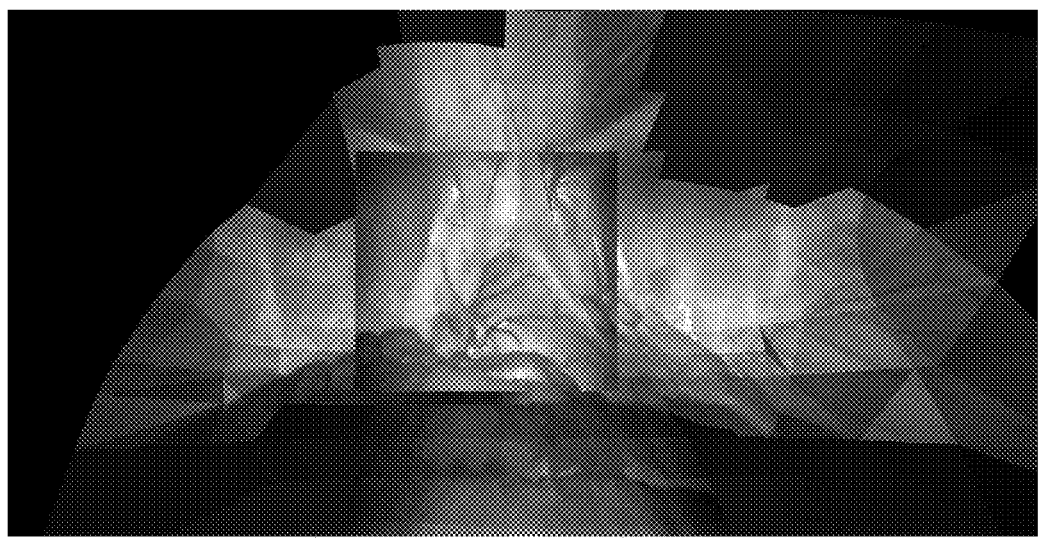
FIG. 11 is an example periphery augmented image that can be displayed during a minimally invasive surgery procedure.

Periphery augmentation can be performed by collecting data of target areas by moving the endoscope and exploring the scene. Simultaneously, the visual SLAM technique can be performed on the endoscopic video to localize the endoscope. Based on the localization results, a three-dimensional vessel network can be recovered and a textured large-area dense reconstruction model can be estimated. While performing periphery augmentation, the endoscope is localized with respect to the recovered textured three-dimensional model and the model is projected back to the camera to generate a virtual view that has a larger field of view than the endoscope and therefore contains peripheral information not captured by the endoscope. In such a case, the central area of the virtual image can comprise the real-time intra-operative image data (e.g., laparoscope video), and the peripheral area of the virtual image can comprise the rendered organs. FIG. 11 illustrates an example of such a virtual image (i.e., peripheral augmentation image).

The invention claimed is:

1. A method for providing augmented reality in minimally invasive surgery, the method comprising:
    capturing pre-operative image data of internal organs of a patient;
    creating a first three-dimensional surface model based upon the captured pre-operative image data, the first three-dimensional surface model comprising a model of a surface of at least one of the internal organs;
    capturing intra-operative image data of the internal organs with an endoscope during a surgical procedure;
    creating a second three-dimensional surface model based on the captured intra-operative image data, the second three-dimensional surface model comprising a model of a surface of at least one of the internal organs;
    registering the three-dimensional surface models in real time during the surgical procedure;
    tracking the position and orientation of the endoscope during the surgical procedure; and
    augmenting the intra-operative image data captured by the endoscope in real time with a rendering of at least a portion of an internal organ of the patient that is in registration with the real time intra-operative image data from the endoscope but outside of the field of view of the endoscope.

2. The method of claim 1, wherein capturing pre-operative image data comprises capturing computed tomography (CT) image data.

3. The method of claim 1, wherein creating a second three-dimensional surface model comprises creating the model using a shadow-based three-dimensional surface reconstruction method in which the model is created based upon shadows cast on surfaces of the internal organs.

4. The method of claim 1, wherein registering the two models comprises registering the models using iterative closest point (ICP) registration.

5. The method of claim 1, wherein tracking the position and orientation of an endoscope comprises tracking the endoscope using a blood vessel-based feature detection method in which branch points and branch segments of blood vessels at the surface of the internal organs are detected.

6. The method of claim 1, wherein the tracking, creating a second three-dimensional surface model, and registering are performed simultaneously in real time during the surgical procedure.

7. The method of claim 6, wherein the tracking and registering are performed by iteratively minimizing both a re-projection error and a registration error in an optimization process.

8. The method of claim 7, wherein the first three-dimensional surface model is used in creating the second three-dimensional surface model and tracking is performed separately in parallel.

9. A non-transitory computer-readable medium that stores an augmented reality program comprising:
    logic configured to create a first three-dimensional surface model of internal organs of a patient based on pre-operative image data;
    logic configured to create a second three-dimensional surface model of the internal organs based on intra-operative image data captured by an endoscope during a surgical procedure;
    logic configured to register the two models in real time during the surgical procedure;
    logic configured to track the position and orientation of the endoscope during the surgical procedure; and
    logic configured to augment the intra-operative image data in real time with a rendering of at least a portion of an internal organ of the patient that is in registration with the real time intra-operative image data from the endoscope but outside of the field of view of the endoscope.

10. The computer-readable medium of claim 9, wherein the logic configured to create a second three-dimensional surface model comprises logic configured to create the model using a shadow-based three-dimensional surface reconstruction method in which the model is created based upon shadows cast on surfaces of the internal organs.

11. The computer-readable medium of claim 9, wherein the logic configured to register the two models comprises logic configured to register the models using iterative closest point (ICP) registration.

12. The computer-readable medium of claim 9, wherein the logic configured to track the position and orientation of an endoscope comprises logic configured to track the endoscope using a blood vessel-based feature detection method in which branch points and branch segments of blood vessels at the surface of the internal organs are detected.

13. The computer-readable medium of claim 9, wherein the logic configured to track, create a second three-dimensional surface model, and register are configured to operate simultaneously in real time during the surgical procedure.

14. The computer-readable medium of claim 13, wherein the logic configured to track and the logic configured to register are simultaneously operated by iteratively minimizing both a re-projection error and a registration error an optimization process.

15. The computer-readable medium of claim 14, wherein logic configured to create the second three-dimensional surface model uses the first three-dimensional surface model in creating the second three-dimensional surface model and the logic configured to track operates separately in parallel.

16. A system for providing augmented reality in minimally invasive surgery, the system comprising:
- a laparoscope configured to capture intra-operative image data of internal organs of a patient during a surgical procedure; and
- a computing device comprising an augmented reality program including:
  - logic configured to create a first three-dimensional surface model of internal organs of a patient based on pre-operative image data,
  - logic configured to create a second three-dimensional surface model of the internal organs based on the intra-operative image data,
  - logic configured to register the two models in real time during the surgical procedure,
  - logic configured to track the position and orientation of the laparoscope during the surgical procedure, and
  - logic configured to augment the intra-operative image data in real time with a rendering of at least a portion of an internal organ of the patient that is in registration with the real time intra-operative image data from the endoscope but outside of the field of view of the laparoscope.

17. The system of claim 16, wherein the logic configured to create a second three-dimensional surface model comprises logic configured to create the model using a shadow-based three-dimensional surface reconstruction method in which the model is created based upon shadows cast on surfaces of the internal organs.

18. The system of claim 16, wherein the logic configured to track the position and orientation of an endoscope comprises logic configured to track the endoscope using a blood vessel-based feature detection method in which branch points and branch segments of blood vessels at the surface of the internal organs are detected.

19. The system of claim 16, wherein the logic configured to track, create a second three-dimensional surface model, and register are configured to operate simultaneously in real time during the surgical procedure.

* * * * *